(12) United States Patent
Koristek et al.

(10) Patent No.: US 8,933,250 B2
(45) Date of Patent: Jan. 13, 2015

(54) PROCESS FOR THE PREPARATION OF N-(1-BENZO[B]THIEN-2-YLETHYL)-N-HYDROXYUREA

(75) Inventors: Kamil Koristek, Samotisky (CZ); Pavel Hradil, Hlusovice (CZ); Martin Grepl, Hlusovice (CZ); Petr Slezar, Olomouc (CZ)

(73) Assignee: Farmak, A.S., Olomouc (CZ)

( * ) Notice: Subject to any disclaimer, the term of this patent is extended or adjusted under 35 U.S.C. 154(b) by 312 days.

(21) Appl. No.: 13/055,463

(22) PCT Filed: Apr. 6, 2009

(86) PCT No.: PCT/CZ2009/000049
§ 371 (c)(1),
(2), (4) Date: Mar. 3, 2011

(87) PCT Pub. No.: WO2010/012246
PCT Pub. Date: Feb. 4, 2010

(65) Prior Publication Data
US 2011/0184189 A1    Jul. 28, 2011

(30) Foreign Application Priority Data
Jul. 31, 2008   (CZ) ..................... 2008-468

(51) Int. Cl.
*C07D 333/58*   (2006.01)
*C07D 333/60*   (2006.01)

(52) U.S. Cl.
CPC ................... *C07D 333/58* (2013.01)
USPC ........................................... 549/58

(58) Field of Classification Search
None
See application file for complete search history.

(56) References Cited

U.S. PATENT DOCUMENTS

| | | |
|---|---|---|
| 4,873,259 A | 10/1989 | Summers, Jr. et al. |
| 5,292,900 A | 3/1994 | Basha et al. |
| 6,080,874 A | 6/2000 | Hengeveld et al. |

FOREIGN PATENT DOCUMENTS

EP      0776898    6/1997

OTHER PUBLICATIONS

Tewari et al., Tetrahedron Letters, 44, 2003, 6639-6642.*
SodiumHydrogenSulfate, 2007, http://web.archive.org/web/20071115225917/http://en.wikipedia.org/wiki/Sodium_bisulfate.*
International Search Report for International Application No. PCT/CZ2009/000049 mailed Sep. 22, 2009.
Copp et al., Acid-catalyzed addition of N-hydroxyurea to 1-aryl alcohol derivatives: a new synthesis of zileuton, Synthetic Communications 2001, vol. 31(20), pp. 3081-3086.
Tewari et al., Amberlite IR-120 catalysed efficient synthesis of glycosyl enamines and their application, Tetrahedron Letters 2003, vol. 44, pp. 6639-6642.
Tewari et al., Tetrabutylammonium hydrogen sulfate catalyzed eco-friendly and efficient synthesis of glycosyl 1,4-dihydropyridines, Tetrahedron Letters 2004, vol. 45, pp. 9011-9014.
Danheiser et al, *Organic Syntheses, Coll.* vol. 5, p. 645 (1973); vol. 40, p. 60 (1960).

* cited by examiner

*Primary Examiner* — Sun Jae Yoo
(74) *Attorney, Agent, or Firm* — Pearl Cohen Zedek Latzer Baratz LLP

(57) ABSTRACT

A method of preparation of N-(1-benzo[b]thien-2-ylethyl)-N-hydroxyurea of formula (I) with the use of a reaction of 1-(benzo[b]thien-2-yl)-ethanol of formula (II) with hydroxyurea of formula (III) in organic solvents, organic acids, their mixtures or in mixtures thereof with water, being catalyzed by strongly acidic cation exchangers or various hydrogen sulphates.

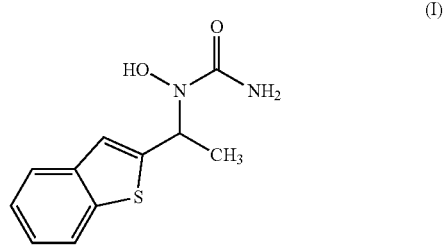

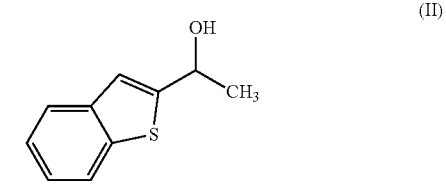

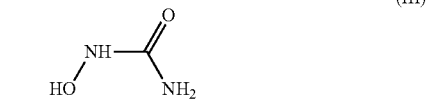

9 Claims, No Drawings

PROCESS FOR THE PREPARATION OF N-(1-BENZO[B]THIEN-2-YLETHYL)-N-HYDROXYUREA

CROSS-REFERENCE TO RELATED APPLICATIONS

This application is a National Phase Application of PCT International Application No. PCT/CZ2009/000049, International Filing Date Apr. 6, 2009, entitled "A PROCESS FOR THE PREPARATION OF N-(1-BENZO[B]THIEN-2-YL-ETHYL)-N-HYDROXYUREA", published on Feb. 4, 2010, as International Publication No. WO 2010/012246, which claims priority of Czech Republic Patent Application No. PV 2008-468, filed on Jul. 31, 2008, both of which are incorporated herein by reference in their entirety.

TECHNICAL FIELD

The invention relates to a new method of preparation of N-(1-benzo[b]thien-2-ylethyl)-N-hydroxyurea of formula I,

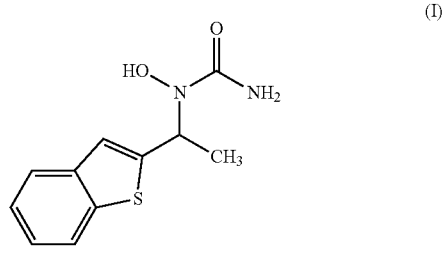 [SMILES: CC(c1cc2ccccc2s1)N(O)C(N)=O]

(I)

which is known as zileuton. It is used for the treatment of asthma, allergies, arthritis and psoriasis as a substance that inhibits biosynthesis of leukotrienes.

BACKGROUND ART

So far several methods of preparation of zileuton of formula I have been described that are contained in patents.

Method (a): (U.S. Pat. No. 4,873,259) Reaction of 2-acetyl-benzo[b]thiophene of formula IV with hydroxylamine producing the oxime of formula V, which should produce the corresponding hydroxylamine of formula VI through reduction by the borane-pyridine complex. The substance of formula VI is then transformed to zileuton of formula I through a reaction either with cyanic acid or trimethylsilyl isocyanate (Scheme 1).

Scheme 1

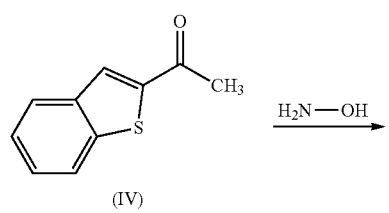

(IV)

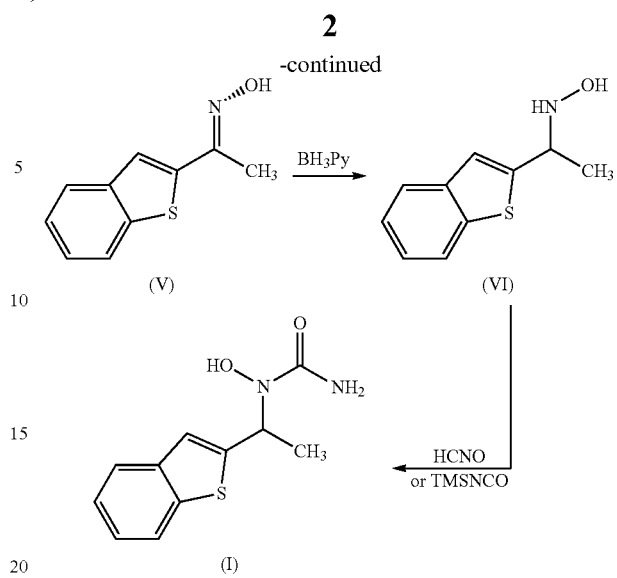

Method (b): (U.S. Pat. No. 4,873,259) Substitution of 1-(benzo[b]thien-2-yl)-1-chloroethane of formula VII with hydroxylamine producing the substance of formula VI, followed by addition to cyanic acid or trimethylsilyl isocyanate (Scheme 2).

Scheme 2

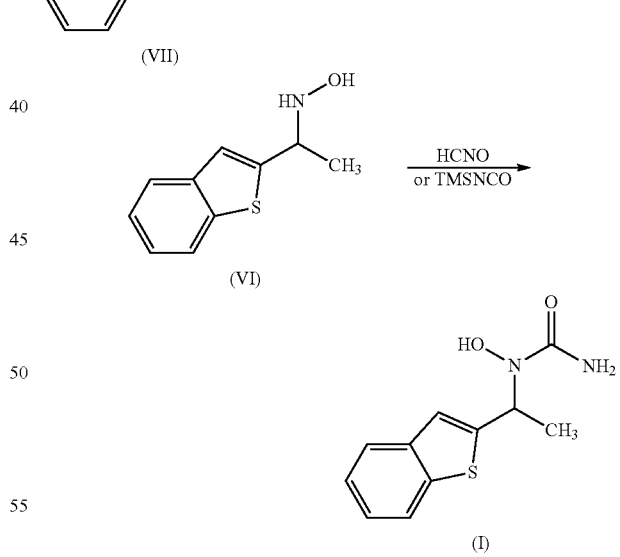

A disadvantage of the above mentioned preparation methods a) and b) is that even by carefully reproducing these methods we did not manage to prepare zileuton.

Method (c): (U.S. Pat. No. 6,080,874) Coupling of 1-(benzo[b]thien-2-yl)-ethanol of formula II with hydroxycarbamide of formula III in an organic solvent in the presence of acids such as hydrochloric, sulphuric, trifluoroacetic and tuloenesulfonic acid (Scheme 3).

Scheme 3

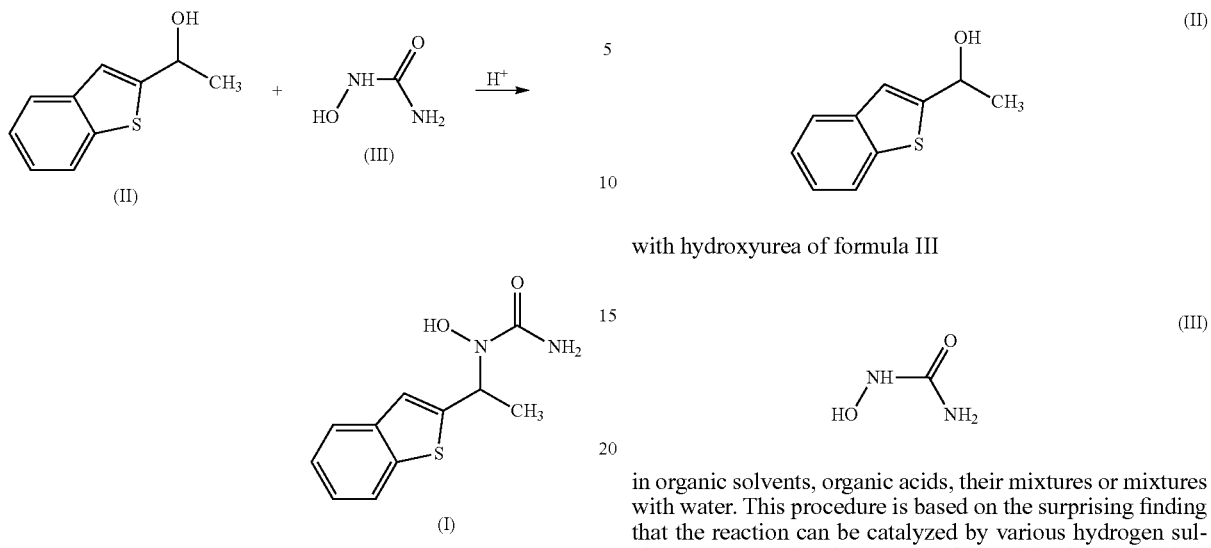

A reproduction of this method provided relatively acceptable results; however, even here some problems were encountered. One of them is high laboriousness of product isolation from the reaction mixture and the resulting relatively low purity and low yield of obtained zileuton. American U.S. Pat. No. 6,080,874 describes general use of acids as the reaction environment. However, when examining this procedure we have found out that the reaction was considerably more complex and the use of acids was not as general as described. The reaction takes place in hydrochloric acid or some other above mentioned acids, but does not take place, or just traces of the product are generated, in case a number of other acids are used, mainly organic acids, e.g. acetic or propionic acid. Also, reactivity is not just the question of pH—e.g. the reaction does not take place if citric acid with pKa of 3.14 or oxalic acid with pKa of 1.25 is used.

The procedure described in U.S. Pat. No. 6,080,874 is laborious and feasible with difficulties; the product is isolated in low yields and with a relatively high content of impurities.

SUBSTANCE OF INVENTION

The object of the invention is a new method of preparation of N-(1-benzo[b]thien-2-ylethyl)-N-hydroxyurea of formula I,

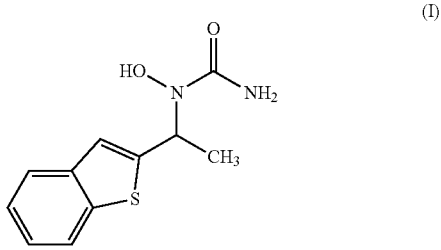 [SMILES: CC(c1cc2ccccc2s1)N(O)C(N)=O]

by reaction of 1-(benzo[b]thien-2-yl)-ethanol of formula II with hydroxyurea of formula III in organic solvents, organic acids, their mixtures or mixtures with water. This procedure is based on the surprising finding that the reaction can be catalyzed by various hydrogen sulphates or may take place successfully with a high yield in a heterogeneous phase while being catalyzed by strongly acidic cation exchangers. Another finding concerns the surprising fact that if a weak organic acid is added to the reaction mixture, e.g. formic acid, acetic acid or propionic acid, a solid product precipitates during neutralization with a relatively high yield as well as acceptable purity (up to 99%). In the development of the new procedure we have concentrated on influencing the yield, achieving the required product purity and significantly simplifying the preparation procedure, mainly the in-situ process by using suitable solvents and catalysts.

Very suitable solvents are organic acids, their mixtures with water or with tetrahydrofuran.

The essence of the invention is that the reaction is performed in the presence of a catalyst in the form of a strongly acidic cation exchanger or various hydrogen sulphates.

In an advantageous embodiment Amberlite IR-120 can be used as the cation exchanger.

In another advantageous embodiment sodium or potassium hydrogen sulphate is used as the hydrogen sulphate.

The essence of the invention also comprises a method of isolation of zileuton from the reaction mixture obtained by a reaction of 1-(benzo[b]thien-2-yl)-ethanol of formula II with hydroxyurea of formula III, which is carried out, after completion of the reaction, by neutralization in the presence of organic acids.

Formic, acetic or propionic acids can advantageously be used as the organic acids.

For the neutralization of the organic acid common bases can be used, such as e.g. alkali or alkaline earth metal carbonates or hydroxides, or ammonium hydroxide, e.g. potassium carbonate, potassium hydroxide, sodium carbonate, sodium hydroxide, and the like.

The method according to the invention has the following advantages:
High yields, which exceed the yields according to the invention (U.S. Pat. No. 4,873,259) by up to 30%;
High purity of substances;
Simple isolation of substances;
Omission of extractions resulting in saving of solvents, reduction of laboriousness and a considerable increase of purity;
A catalytic quantity of the hydrogen sulphate can be beneficially prepared in situ.

EXAMPLES

The essence of the procedure according to the present invention is illustrated in more detail in the following examples. These examples only have an illustrative character and do not limit the scope of the invention in any way.

Example 1

To 0.4 g (5.33 mmol) of methyl carbamate 0.39 g (5.87 mmol) of a 50% aqueous solution of hydroxylamine was added and the mixture was stirred until complete dissolution at the room temperature. Then, under cooling 0.3 ml (5.77 mmol) of a 50% aqueous solution of sodium hydroxide was added dropwise in such a way to maintain the temperature of the reaction mixture in the range of 5 to 30° C. After that, the temperature was reduced to 20 to 25° C. and the mixture was stirred for another 4 hours. To the syrup obtained this way 2 ml of tetrahydrofuran, 0.47 g (2.67 mmol) of 2-acetylbenzo[b]thiophene, 62 mg (1.64 mmol) of sodium tetrahydroborate and finally 0.38 ml of methanol were added under cooling at such a rate to maintain the temperature of the reaction mixture between 10 and 40° C. After the addition of methanol the mixture was stirred at the temperature of 20 to 25° C. for another 75 minutes.

2 ml of acetic acid and 2 ml of concentrated hydrochloric acid were added and the reaction mixture was stirred for 3 hours at the temperature of 40 to 45° C. Then, it was cooled to 20 to 25° C., neutralized with 15 ml of a 10% aqueous solution of sodium hydroxide to pH=7 and cooled to the temperature of 20 to 25° C. The separated precipitate was stirred for another 15 minutes at the temperature of 20 to 25° C., filtered off and gradually washed on the filter with 20 ml of water, 6.5 ml of toluene, again with 5 ml of water and finally with 2 ml of toluene. After drying in a hot-air drier at 80 to 85° C. 0.55 g of colourless crystalline powder of N-(1-benzo[b]thien-2-ylethyl)-N-hydroxyurea was isolated in the yield of 88% with HPLC purity of 99%.

Example 2

To a mixture of 0.2 g (2.63 mmol) of hydroxyurea, 0.288 g (1.62 mmol) of 1-(benzo[b]thien-2-yl)-ethanol, 2 ml of tetrahydrofuran and 1 ml of water 1.57 g of the Amberlite IR-120 ion exchanger were added and the reaction mixture was intensively stirred at the boiling temperature for 180 hours. After this time period the conversion of the initial ketone to zileuton was determined to be 71% by means of HPLC.

Example 3

To a mixture of 0.1 g (1.31 mmol) of hydroxyurea, 0.144 g (0.808 mmol) of 1-(benzo-[b]thien-2-yl)-ethanol, 2 ml of acetic acid and 0.5 ml of water 1.1 g of the Amberlite IR-120 ion exchanger were added and the reaction mixture was intensively stirred at the temperature of 40 to 45° C. for 7 hours altogether. After this time period the conversion of the initial ketone to zileuton was determined to be 85% by means of HPLC.

Example 4

A mixture of 0.1 g (1.31 mmol) of hydroxyurea, 0.144 g (0.808 mmol) of 1-(benzo[b]thien-2-yl)-ethanol, 2 ml of acetic acid and 0.5 ml of water was stirred at the temperature of 40 to 45° C. After 6 hours no zileuton is generated according to HPLC. To the reaction mixture 0.59 g of the Amberlite IR-120 ion exchanger was added and the mixture was further stirred at the temperature of 40 to 45° C. After 6 hours 65% conversion to zileuton was achieved (according to HPLC). After another 7 hours 81% conversion was achieved.

Example 5

A mixture of 0.1 g (1.31 mmol) of hydroxyurea, 0.144 g (0.808 mmol) of 1-(benzo[b]thien-2-yl)-ethanol, 2 ml of acetic acid and 0.5 ml of water was heated up to the boiling temperature (118° C.). After 5 hours no zileuton was identified by means of HPLC. The reaction mixture only contained 65% of the initial 1-(benzo[b]thien-2-yl)-ethanol and the rest consisted of impurities.

Example 6

A mixture of 1 g (13.1 mmol) of hydroxyurea, 1.44 g (8.08 mmol) of 1-(benzo[b]thien-2-yl)-ethanol, 20 ml of acetic acid, 5 ml of water and 1.1 g (8.08 mmol, 1 eq.) of potassium hydrogen sulphate was stirred at the temperature of 40 to 45° C. After 6 hours the reaction was terminated and the reaction mixture was diluted with 100 ml of water, neutralized with 40 ml of 10% sodium hydroxide, the separated precipitate was filtered off, washed with 20 ml of water and then with 5 ml of toluene. After drying in a hot-air drier 1.56 g (82%) of colourless zileuton powder was obtained with the HPLC purity higher than 95%.

Example 7

A mixture of 0.1 g (1.31 mmol) of hydroxyurea, 0.144 g (0.808 mmol) of 1-(benzo[b]thien-2-yl)-ethanol, 2 ml of propionic acid and 0.5 ml of water was stirred at the temperature of 40 to 45° C. Even after 10 hours no zileuton was detected by means of HPLC. The reaction mixture was heated up to boiling (141° C.). Even after 3.5 hours of boiling no zileuton was found by means of HPLC.

Example 8

A mixture of 0.1 g (1.31 mmol) of hydroxyurea, 0.144 g (0.808 mmol) of 1-(benzo[b]thien-2-yl)-ethanol, 2 ml of propionic acid, 0.5 ml of water and 1.26 g of the Amberlite IR-120 ion exchanger was stirred at the temperature of 40 to 45° C. After 5 hours the initial 1-(benzo[b]thien-2-yl)-ethanol was converted by the reaction according to HPLC. After a total of 6 hours at the temperature of 40 to 45° C. the reaction was terminated, the ion exchanger was filtered off and the filtrate neutralized with 4 ml of 10% sodium hydroxide. The separated precipitate of the product was removed by filtration, washed with water (10 ml) and then with 5 ml of toluene. After drying in a hot-air drier 0.16 g (80%) of colourless zileuton powder was obtained with the HPLC purity of 98%.

Example 9

A mixture of 0.1 g (1.31 mmol) of hydroxyurea, 0.144 g (0.808 mmol) of 1-(benzo[b]thien-2-yl)-ethanol, 2 ml of propionic acid, 0.5 ml of water and 0.55 g (4.04 mmol, 5 eq.) of potassium hydrogen sulphate was stirred at the temperature of 40 to 45° C. After a total of 6 hours at the temperature of 40 to 45° C. the reaction was terminated, the conversion to zileuton was 91% according to HPLC.

Example 10

A mixture of 0.1 g (1.31 mmol) of hydroxyurea, 0.144 g (0.808 mmol) of 1-(benzo[b]thien-2-yl)-ethanol, 2 ml of methanol, 0.5 ml of water and 1.26 g of the Amberlite IR-120 ion exchanger was stirred at the boiling temperature for 20 hours. After the expiration of this time period 86% conversion to zileuton was confirmed.

Example 11

A mixture of 0.1 g (1.31 mmol) of hydroxyurea, 0.144 g (0.808 mmol) of 1-(benzo[b]thien-2-yl)-ethanol, 2 ml of tetrahydrofuran, 2 ml of water and 0.51 g (1.04 mmol, 5 eq.) of oxalic acid dihydrate was stirred at the temperature of 40 to 45° C. for 6 hours. After the expiration of this time period no zileuton was found.

Example 12

To 0.8 g (10.66 mmol) of methyl carbamate 0.78 g (11.81 mmol) of a 50% aqueous solution of hydroxylamine was added and the mixture was stirred at the room temperature until complete dissolution. Then, under cooling 0.6 ml (11.54 mmol) of a 50% aqueous solution of sodium hydroxide was added dropwise in such a way to maintain the temperature of the reaction mixture in the range of 5 to 30° C. Then, the temperature was adapted to 20 to 25° C. and the mixture was stirred for another 4 hours. To the syrup obtained this way 4 ml of tetrahydrofuran, 0.94 g (5.34 mmol) of 2-acetylbenzo[b]thiophene, 0.124 g (3.28 mmol) of sodium tetrahydroborate and finally 0.76 ml of methanol were added under cooling at such a rate to maintain the temperature of the reaction mixture between 10 and 40° C. After the addition of methanol the mixture was stirred at the temperature of 20 to 25° C. still for 1 hour.

To the obtained mixture 4 ml of formic acid and 0.79 ml (14.82 mmol) of sulphuric acid were added under cooling at the temperature of 5-45° C., the sulphuric acid having converted all the sodium ions coming from sodium hydroxide and sodium tetrahydroborate in the reaction mixture to sodium hydrogen sulphate. Then, the reaction mixture was stirred at the temperature of 40 to 45° C. for another 6 hours. Then, it was cooled to 20 to 25° C., neutralized with 25 ml of a 10% aqueous solution of sodium hydroxide to pH=7 and cooled to the temperature of 0 to 5° C. The separated precipitate was stirred at the temperature of 0 to 5° C. for another 10 minutes, filtered off and gradually washed twice with 10 ml of water and then twice with 10 ml of toluene on the filter. After drying in a hot-air drier at 80 to 85° C. 1.02 g (81%) of zileuton was obtained.

Example 13

To 0.8 g (10.66 mmol) of methyl carbamate 0.78 g (11.81 mmol) of a 50% aqueous solution of hydroxylamine was added and the mixture was stirred until complete dissolution at the room temperature. Then, 0.6 ml (11.54 mmol) of a 50% aqueous solution of sodium hydroxide was added dropwise under cooling in such a way to maintain the temperature of the reaction mixture in the range of 5 to 30° C. Then, the temperature was adapted to 20 to 25° C. and the mixture was stirred for another 4 hours. To the syrup obtained this way 4 ml of tetrahydrofuran, 0.94 g (5.34 mmol) of 2-acetylbenzo[b]thiophene, 0.124 g (3.28 mmol) of sodium tetrahydroborate and finally 0.76 ml of methanol were added under cooling at such a rate to maintain the temperature of the reaction mixture between 10 and 40° C. After the addition of methanol the mixture was stirred at the temperature of 20 to 25° C. for 1 hour.

To the obtained mixture 4 ml of formic acid were added under cooling at the temperature of 5 to 45° C. and the resulting solution was stirred at the temperature of 40 to 45° C. for 6 hours altogether. Even after this time period no zileuton was detected. Therefore, another 4 ml of formic acid were added to the reaction mixture and it was stirred at the temperature of 40 to 45° C. for 6 hours. No occurrence of zileuton was observed.

Example 14

Purification

Crude zileuton 0.79 g (3.34 mmol) obtained according to Example 1 was dissolved in a mixture of 2.19 ml (8.35 mmol) of 10% aqueous sodium hydroxide and 8 ml of water at the room temperature The obtained solution was extracted with 4 ml of toluene. After separation the toluene layer was removed and 0.1 of active carbon was added to the obtained aqueous layer and it was stirred for 10 minutes. The carbon was filtered off, 0.7 ml of acetic acid was added to the clear filtrate and the obtained suspension was stirred at the temperature of 20 to 25° C. for another 15 minutes. The separated product was filtered off, washed with 10 ml of water and dried in a hot-air drier at the temperature of 80 to 85° C. 0.71 g (90%) of colourless, crystalline N-(1-benzo[b]thien-2-ylethyl)-N-hydroxyurea was obtained with the HPLC purity of 99.9%. The content of no impurity is higher than 0.1%.

Industrial Applicability

The method of preparation of N-(1-benzo[b]thien-2-ylethyl)-N-hydroxyurea of formula I according to the invention can be applied in advantageous technological-economical conditions while maintaining high yield under mild reaction conditions.

The invention claimed is:

1. A process for the preparation of N-(1-benzo[b]thien-2-ylethyl)-N-hydroxyurea of formula I

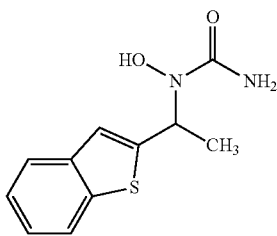

(I)

comprising the steps of:
preparing hydroxyurea of formula III;

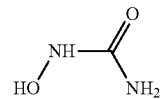

(III)

preparing 1-(benzo[b]thien-2-yl)-ethanol of formula II

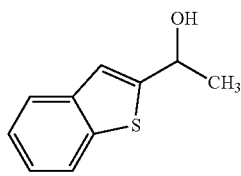

in the same pot; and adding at least one of tetrahydrofuran, methanol, formic acid or acetic acid or any combination thereof with or without water; and catalysing by sodium hydrogen sulphate.

2. The process according to claim 1, wherein the sodium hydrogen sulphate is produced by reacting an aqueous solution of sodium hydroxide with suphuric acid.

3. The process according to claim 1, further comprising the isolation of the compound of Formula I from a reaction mixture of 1-(benzo[b]thien-2-yl)-ethanol of formula II with hydroxyurea of formula III, wherein the compound of Formula I is isolated from the reaction mixture after termination of the reaction by neutralization in the presence of an organic acid.

4. The process according to claim 3, wherein the organic acid is formic or acetic acid.

5. The process according to claim 1, wherein tetrahydrofuran and methanol are added.

6. The process according to claim 1, wherein formic acid is added.

7. The process according to claim 1, wherein tetrahydrofuran, methanol, formic acid and sodium hydrogen sulfate are added.

8. The process according to claim 1, wherein the sodium hydrogen sulfate is made by mixing sodium hydroxide and sodium tetrahydroborate with a stoichiometric amount of sulphuric acid.

9. The process according to claim 7, wherein the sodium hydrogen sulfate is made by mixing sodium hydroxide and sodium tetrahydroborate with a stoichiometric amount of sulphuric acid.

* * * * *